US012714879B2

(12) United States Patent
Tallinen et al.

(10) Patent No.: US 12,714,879 B2
(45) Date of Patent: Aug. 25, 2026

(54) APPARATUS AND METHOD FOR FACILITATING OPTIMIZATION OF A RADIATION TREATMENT PLAN FOR A PARTICULAR PATIENT USING AT LEAST ONE MULTI-LEAF COLLIMATOR

(71) Applicant: Siemens Healthineers International AG, Steinhausen (CH)

(72) Inventors: Tuomas Tallinen, Espoo (FI); Mirko Myllykoski, Helsinki (FI); Marko Rusanen, Espoo (FI)

(73) Assignee: Siemens Healthineers International AG, Steinhausen (CH)

(*) Notice: Subject to any disclaimer, the term of this patent is extended or adjusted under 35 U.S.C. 154(b) by 204 days.

(21) Appl. No.: 18/368,183

(22) Filed: Sep. 14, 2023

(65) Prior Publication Data

US 2025/0090864 A1 Mar. 20, 2025

(51) Int. Cl.
*A61N 5/10* (2006.01)

(52) U.S. Cl.
CPC ......... *A61N 5/1036* (2013.01); *A61N 5/1045* (2013.01); *A61N 5/1048* (2013.01); *A61N 2005/1074* (2013.01)

(58) Field of Classification Search
None
See application file for complete search history.

(56) References Cited

U.S. PATENT DOCUMENTS

2011/0051893 A1* 3/2011 McNutt ................ A61N 5/1031 600/407
2011/0122997 A1* 5/2011 Lu ........................ A61N 5/1042 378/65
2014/0235923 A1* 8/2014 McNutt ................ A61N 5/1071 600/1
2014/0348288 A1* 11/2014 Boyd ..................... A61B 6/405 378/4
2017/0042489 A1* 2/2017 Boyd ..................... A61B 6/025
2018/0021594 A1* 1/2018 Papp ...................... A61N 5/103 600/1
2020/0306559 A1* 10/2020 Kuusela ............... A61N 5/1043
2021/0205635 A1* 7/2021 Bokrantz ............ A61N 5/1031
2022/0047893 A1* 2/2022 Wen ...................... A61N 5/1031
2022/0241612 A1* 8/2022 Wen ...................... A61N 5/1047

OTHER PUBLICATIONS

Extended European Search Report from related European Patent Application No. 24194374.5 dated Feb. 7, 2025; 8 pages.

(Continued)

*Primary Examiner* — Marcus H Taningco
(74) *Attorney, Agent, or Firm* — Fitch, Even, Tabin & Flannery LLP

(57) ABSTRACT

A control circuit that is configured as a graphics processing unit optimizes leaf movements for at least one multi-leaf collimator, and where optimizing the leaf movements is configured as a highly parallel optimization opportunity. By one approach, a second control circuit serves, at least in part, to so configure the optimizing of the leaf movements as the highly parallel optimization opportunity. That second control circuit can itself be configured as a central processing unit (as distinct from, for example, the aforementioned graphics processing unit).

16 Claims, 5 Drawing Sheets

(56) References Cited

OTHER PUBLICATIONS

Galanakou, Panagiota et al.; A parallelized GPU-based simulating annealing algorithm for intensity modulated radiation therapy optimization; 2017 18TH IEEE/ACIS International Conference on Software Engineering, Artificial Intelligence, Networking and Parallel/ Distributed Computing (SNPD), IEEE, Jun. 26, 2017 (Jun. 26, 2017), pp. 345-350.

Kalantzis, Georgios et al.; Investigations of a GPU-based levy-firefly algorithm for constrained optimization of radiation therapy treatment planning; Swarm and Evolutionary Computation, vol. 26, Feb. 1, 2016 (Feb. 1, 2016), pp. 191-201.

Men, Chunhua et al.; GPU-based ultra-fast direct aperture optimization for online adaptive radiation therapy;GPU-based ultrafast DAO for online adaptive radiation therapy; Physics in Medicine and Biology, Institute of Physics Publishing, Bristol GB, vol. 55, No. 15, Jul. 20, 2010 (Jul. 20, 2010), pp. 4309-4319.

Tian, Zhen et al.; Multi-GPU implementation of a VMAT treatment plan optimization algorithm, Medical Physics, AIP, Melville, NY, US, vol. 42, No. 6, May 18, 2015 (May 18, 2015), pp. 2841-2852.

* cited by examiner

APPARATUS AND METHOD FOR FACILITATING OPTIMIZATION OF A RADIATION TREATMENT PLAN FOR A PARTICULAR PATIENT USING AT LEAST ONE MULTI-LEAF COLLIMATOR

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

The foregoing can include optimizing the adjustments and usage of one or more multi-leaf collimators. Unfortunately, optimizing the movements and use of a multi-leaf collimator often comprises a significant part of the overall optimization process and can contribute significantly to the overall length of time required to create an optimized radiation treatment plan. For example, some optimization algorithms include a recurring sub step in which the optimizer attempts to find a leaf sequence (i.e., a set of control points) that matches a given target fluence as closely as possible while complying with given leaf movement limits. In the context of a serially-computed optimization approach, the latter leaf sequence optimization can consume a disproportionate amount of time in comparison to the overall optimization sequence.

BRIEF DESCRIPTION OF THE DRAWINGS

The above needs are at least partially met through provision of the apparatus and method for facilitating optimization of a radiation treatment plan for a particular patient using at least one multi-leaf collimator that is described in the following detailed description, particularly when studied in conjunction with the drawings, wherein.

Figure 1:
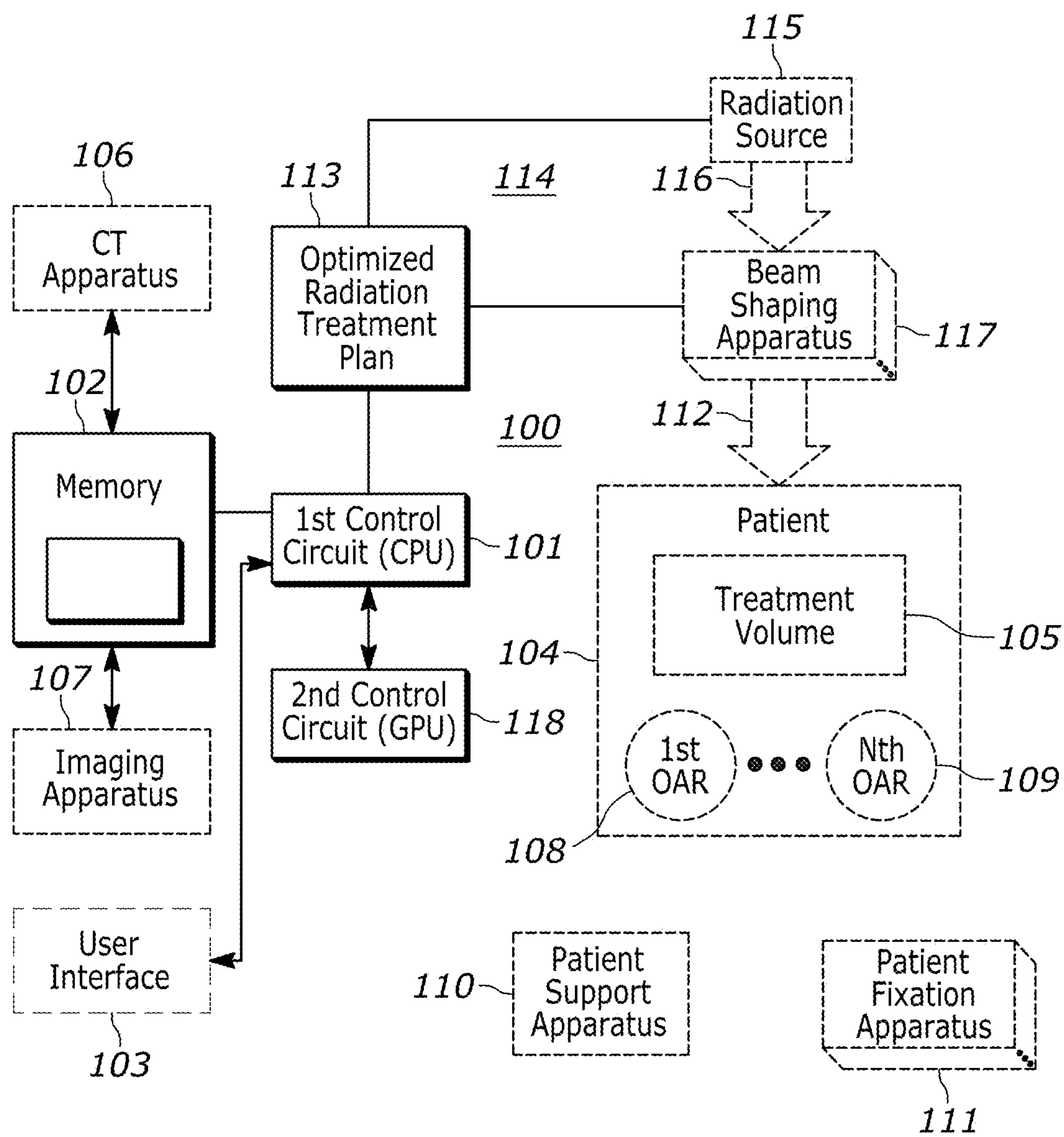
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate optimizing a radiation treatment plan for a particular patient using at least one multi-leaf collimator. Generally speaking, these teachings provide for optimizing leaf movements for the at least one multi-leaf collimator using a control circuit that is configured as a graphics processing unit, and where optimizing the leaf movements is configured as a highly parallel optimization opportunity. By one approach, a second control circuit serves, at least in part, to so configure the optimizing of the leaf movements as the highly parallel optimization opportunity. That second control circuit can itself be configured as a central processing unit (as distinct from, for example, the aforementioned graphics processing unit). So configured, the second control circuit can undertake the overall task of optimizing a radiation treatment plan while appropriately being informed by the graphics processing unit with optimization information for the leaf sequencing.

By one approach, the graphics processing unit can be configured to optimize the leaf movements as a function of at least one metaheuristic approach. By one approach, that metaheuristic approach can comprise a differential evolution approach. If desired, the latter can comprise using differential evolution-specific parameters that include an iteration count of about 100 iterations and a population size of about 50 agents.

By another approach, in lieu of the foregoing or in combination therewith, the graphics processing unit can be configured to optimize the leaf movements as a function of at least one parallel explicit integration approach. If desired, the latter can comprise determining forces acting on each leaf (that is, "pseudo" forces that fit the leaves to the fluence, rather than the forces that move the leaves physically) of the at least one multi-leaf collimator as a function, at least in part, of determined fluence under each of the leaves and from constraints between the leaves in adjacent control points, and then updating velocities and positions of the leaves as a function of the forces. By one approach, fluence can be assumed to be continuous when so determining the forces.

When optimizing using both of the foregoing approaches, if desired, these teachings will accommodate optimizing the leaf movements as a function of first optimizing as a function of the at least one metaheuristic approach and then subsequently optimizing as a function of the at least one parallel explicit integration approach.

So configured, leaf optimization can be accomplished via highly parallelized approaches that are readily implemented on, and take advantage of, the processing capabilities of a graphics processing unit.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a first control circuit 101. Being a "circuit," the first control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

This first control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This first control circuit 101 is configured (for example, by using corresponding programming as will be well understood by those skilled in the art) to carry out one or more of the steps, actions, and/or functions described herein.

For the purposes of illustration, this description will presume this first control circuit to be configured as a central control unit (CPU). Central processing units comprise the primary hardware component of a computer system and are responsible for executing instructions and performing calculations. CPUs interpret and execute a sequence of instructions from one or more software programs to perform tasks and manipulate data. CPUs typically include a number of components including a control unit (that manages the execution of instructions by fetching instructions from the computer's memory, decoding those instructions to understand their meaning, and then coordinating the various other components of the CPU to carry out the instructions), an arithmetic logic unit (ALU) (which is responsible for performing arithmetic calculations (such as addition, subtraction, multiplication, and division) and logical operations (like AND, OR, NOT) as specified by the aforementioned instructions; The ALU is usually the core computational component of the CPU), registers (which are small, high-speed memory units located within the CPU that store data and intermediate results during processing and make data quickly accessible to the CPU without having to retrieve it from slower main memory such as random access memory), cache memory (which is a small, high-speed memory located on or near the CPU and which stores frequently used data and instructions to reduce the time the CPU needs to access that content as compared to the slower main memory; caches come in different levels (L1, L2, L3) with varying sizes and speeds), a clock (which provides a clock signal that synchronizes the activities of the CPU, the clock signal typically comprising a steady rhythm of pulses, each pulse representing a discrete unit of time (clock cycle); the speed of the clock, usually measured in Hertz, determines how many instructions the CPU can execute per second), and, at least in modern CPUs, at least one pipeline within which instructions are broken down into smaller stages, and multiple instructions can be in different stages of processing simultaneously to improve throughput and make use of available resources more effectively.

The first control circuit 101 operably couples to a memory 102. This memory 102 may be integral to the first control circuit 101 or can be physically discrete (in whole or in part) from the first control circuit 101 as desired. This memory 102 can also be local with respect to the control circuit 101 (where, for example, both share a common circuit board, chassis, power supply, and/or housing) or can be partially or wholly remote with respect to the first control circuit 101 (where, for example, the memory 102 is physically located in another facility, metropolitan area, or even country as compared to the first control circuit 101).

In addition to information such as optimization information for a particular patient and information regarding a particular radiation treatment platform as described herein, this memory 102 can serve, for example, to non-transitorily store the computer instructions that, when executed by the first control circuit 101, cause the first control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the first control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the first control circuit 101 can also operably couple to a network interface (not shown). So configured the first control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the first control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the first control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the first control circuit 101. As the foregoing elements and systems are well understood in the art, further elaboration in these regards is not provided here except where otherwise relevant to the description.

In this illustrative example the apparatus 100 also includes a second control circuit 118 that operably couples to and interacts with the aforementioned first control circuit 101. In this example this second control circuit 118 is configured as a graphics processing unit (GPU). A GPU is a specialized hardware component typically designed for rendering and processing graphics and visual data. Unlike a CPU, which is more versatile and handles a wider range of tasks, a GPU is optimized specifically for parallel processing tasks that often serve well in graphics-intensive applications such as gaming, three-dimensional rendering, video editing, and scientific simulations. A number of characteristics and components of a typical GPU include:

Parallel Architecture: A GPU contains a large number of smaller processing units called cores or stream processors. These cores work simultaneously on different parts of a task, enabling the GPU to perform many calculations at once.

CUDA/OpenCL: Many modern GPUs support programming languages like CUDA (Compute Unified Device Architecture) for NVIDIA-manufactured GPUs and OpenCL (Open Computing Language) for a variety of GPU brands. These programming models allow developers to apply the GPU's parallel processing capabilities for non-graphical tasks such as scientific simulations and machine learning.

Memory: GPUs typically have their own dedicated high-speed memory, often called video memory or VRAM. This high-speed memory can serve, for example, to store textures, framebuffers, and other graphical data needed for graphics rendering. VRAM's quick access speed supports speedy rendering of high-resolution graphics without bottlenecking the system's overall performance.

APIs (Application Programming Interfaces): GPUs are typically controlled using APIs like DirectX (for Windows) and OpenGL (cross-platform). These APIs provide a standardized way for software in, for example, the aforementioned first control circuit 101 to communicate with and utilize the GPU's capabilities.

By one approach, this second control circuit 118, configured as a GPU, can be built into the same chip as the first control circuit 101 that serves as a CPU, in which case, if desired, these two control circuits can share at least some system memory. Dedicated GPUs (i.e., circuits having their own separate chip with their own on-board memory), however, tend to offer significantly better performance for many parallel-processing intensive tasks.

In the present illustrative example, the GPU is not used (at least not primarily) to do graphics processing. Instead, the present teachings leverage the parallel architecture of the GPU to accelerate calculations regarding optimization of a multi-leaf collimator as described herein that would be time-consuming on the first control circuit (that is configured as a CPU).

Figure 2:
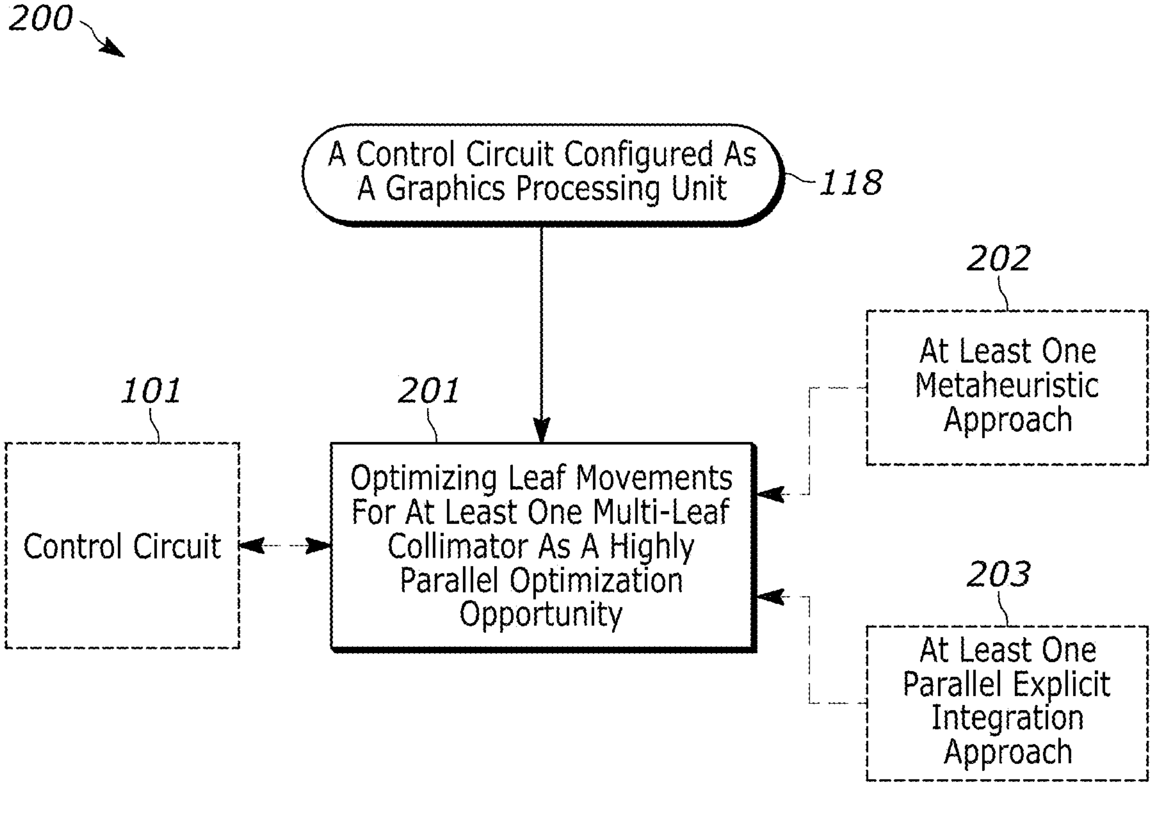
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned second control circuit 118) will be described. Generally speaking, this process 200 serves to facilitate optimizing leaf movements for one or more multi-leaf collimators as part of optimizing a radiation treatment plan for a particular patient with therapeutic radiation using a particular radiation treatment platform.

At block 201, this process 200 optimizes leaf movements for at least one multi-leaf collimator that comprises a part of the aforementioned beam shaping apparatus 117. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically, the leaves of a multi-leaf collimator are organized in pairs that are aligned collinearly with respect to one another and which can selectively move towards and away from one another. A typical multi-leaf collimator has many such pairs of leaves, often upwards of twenty, fifty, or even one hundred such pairs.

With the second control circuit 118 being configured as a GPU, the GPU undertakes that optimizing task as a highly parallel optimization opportunity.

By one optional approach, this optimizing takes place under the overall control of the aforementioned first control circuit 101 (which is, in this example, configured as a CPU). So configured, the second control circuit 118 undertakes the appropriate calculations for optimizing leaf movements when and as needed by the first control circuit 101, using information provided thereby and providing its optimization results thereto.

These teachings will accommodate so leveraging the second control circuit 118 (configured as a GPU) using any of a variety of approaches. As one example, the GPU can be configured to optimize the leaf movements as a function of at least one of at least one metaheuristic approach 202 and at least one parallel explicit integration approach 203. More specifically, the GPU can employ one or the other of those two approaches, or, if desired, can employ both such approaches. When using both approaches, these teachings will accommodate, for example, first optimizing as a function of at least one metaheuristic approach 202 and then subsequently optimizing as a function of at least one parallel explicit integration approach, in that order.

By one approach, when using the metaheuristic approach 202, the latter may comprise, at least in part, a differential evolution approach. The latter, in turn, may comprise, if desired, use of differential evolution-specific parameters that include an iteration count of about 100 iterations and a population size of about 50 agents. (As used in the foregoing sentence, the word "about" will be understood to represent a range of plus or minus some selected threshold, such as five percent, ten percent, fifteen percent, or twenty-five percent as desired.)

By one approach, when using the parallel explicit integration approach 203, the latter may comprise, at least in part, determining pseudo forces corresponding to each leaf of the one or more multi-leaf collimators as a function, at least in part, of determined fluence under each of the leaves and from constraints between the leaves in adjacent control points, and then updating velocities and positions of the leaves as a function of those forces. By one approach, the fluence can be assumed to be continuous when so determining those forces. (Fluence, of course, represents radiative flux integrated over time and comprises a fundamental metric in dosimetry (i.e., the measurement and calculation of an absorbed dose of ionizing radiation in matter and tissue).)

Further details that comport with these teachings will now be presented. It will be understood that the specific details of these examples are intended to serve an illustrative purpose and are not intended to suggest any particular limitations with respect to these teachings.

Metaheuristic Approaches

A metaheuristic approach can simultaneously work on a set of solution candidates and hence simplify core computational operations. Such an approach need make few or no assumptions about the underlying optimization problem and can search a very large solution space without getting stuck in a local optimal solution. Although a metaheuristic approach can be much more computationally demanding than a special-purpose algorithm, the applicant has determined that the significantly increased parallelism can offset this downside. Several metaheuristic algorithms are known in the art. The following examples presume the use of differential evolution, and in particular, box-standard differential evolution.

A box-standard differential evolution algorithm first generates a population of agents (that is, solution candidates) at random: $P=\{x:x\in\mathbb{R}^n\}$. During an iteration, each agent $x\in P$ is mutated by combining it with three other agents, a, b, $c\in P$, using an element-wise mutation formula:

$$y_i = \begin{cases} a_i + F\times(b_i - c_i), & \text{if } r_i < CR, \\ x_i, & \text{otherwise,} \end{cases}$$

where $F\in[0, 2]$, $r_i\sim U(0,1)$, and $CR\in[0, 1]$. Each mutated agent y is then evaluated using a given cost function Cost: $\mathbb{R}^n\rightarrow\mathbb{R}$ and the original agent x is replaced by the mutated agent y if the later is found to have a lower associated cost:

$$x \leftarrow \begin{cases} y, & \text{if Cost}(y) < \text{Cost}(x), \\ x, & \text{otherwise.} \end{cases}$$

The basic differential evolution algorithm is convenient to implement and parallelize as only the cost function needs to know how the agents are encoded. The applicant has determined, however, that by one approach, four application-area-specific components can be beneficially carefully chosen and/or implemented for the differential evolution algorithm to work efficiently. These components include differential evolution-specific parameters (in particular, iteration count, population size, differential weight F, and crossover probability CR), the cost function, initial population generation, and optional postprocessing.

In this example, the aforementioned four differential evolution-specific parameters were chosen through experimentation. For performance reasons, both the iteration count and the population size were kept relatively small (for example, about 100 iterations with 50 agents). The differential weight F, which is part of the mutation formula, was chosen to be a relatively modest 0.15 but the optimal value can depend on how the population is initialized. The crossover probability CR, which defines the element-wise mutation probability, was chosen to be 0.9 (such that 90% of the elements are mutated).

In this example, target fluence fitting, monitor unit (MU) smoothing, and leaf movement limits (for example, between adjacent sectors, adjacent control points, and adjacent leaves) were integrated to the cost function as separate objectives:

$$\text{Cost}(x) = w_1 Obj_{fitting}(x) + w_2 Obj_{MU}(x) + w_3 Obj_{sector}(x) + w_4 Obj_{CP}(x) + w_5 Obj_{leaf}(x).$$

So configured, new objectives can be added without modifying the optimizer itself. Both the leave positions and the per-control point monitor units can be encoded to the agents (i.e., the optimizer optimizes both the leaf positions and the per-control point monitor units). The cost calculation is done in a highly parallel manner as the sectors (where each sector in this example comprises a plurality of control points and where each sector has its own population), the agents, the leaves, and the fluence pixels can be processed independently of each other (excluding fast reduction operations).

The differential evolution algorithm can be sensitive to the way the initial population is generated. It is possible to start from a completely randomly generated initial population but convergence to a good-quality global solution may in that case require thousands of iterations and very careful tuning of the objective weights. On the other hand, an initial population consisting of simple conforming leaf openings does not contain enough variation and can therefore lead to a poor-quality local solution.

The applicant has determined that, to reach sufficient performance and a satisfactory result, the initial population can be generated by fitting individual leaves to the target fluence in a greedy manner. (In the context of differential evolution, the word "greedy" refers to an algorithm that follows the problem-solving heuristic of making the locally optimal choice at each stage. In many problems, a greedy strategy does not produce an optimal solution, but a greedy heuristic can yield locally optimal solutions that approximate a globally optimal solution in a reasonable amount of time.) The initial monitor units are chosen at random (from a distribution that matches the target fluence's value distribution), control points are traversed in two opposite orders, and the fitting begins from two opposite directions.

Figure 3:
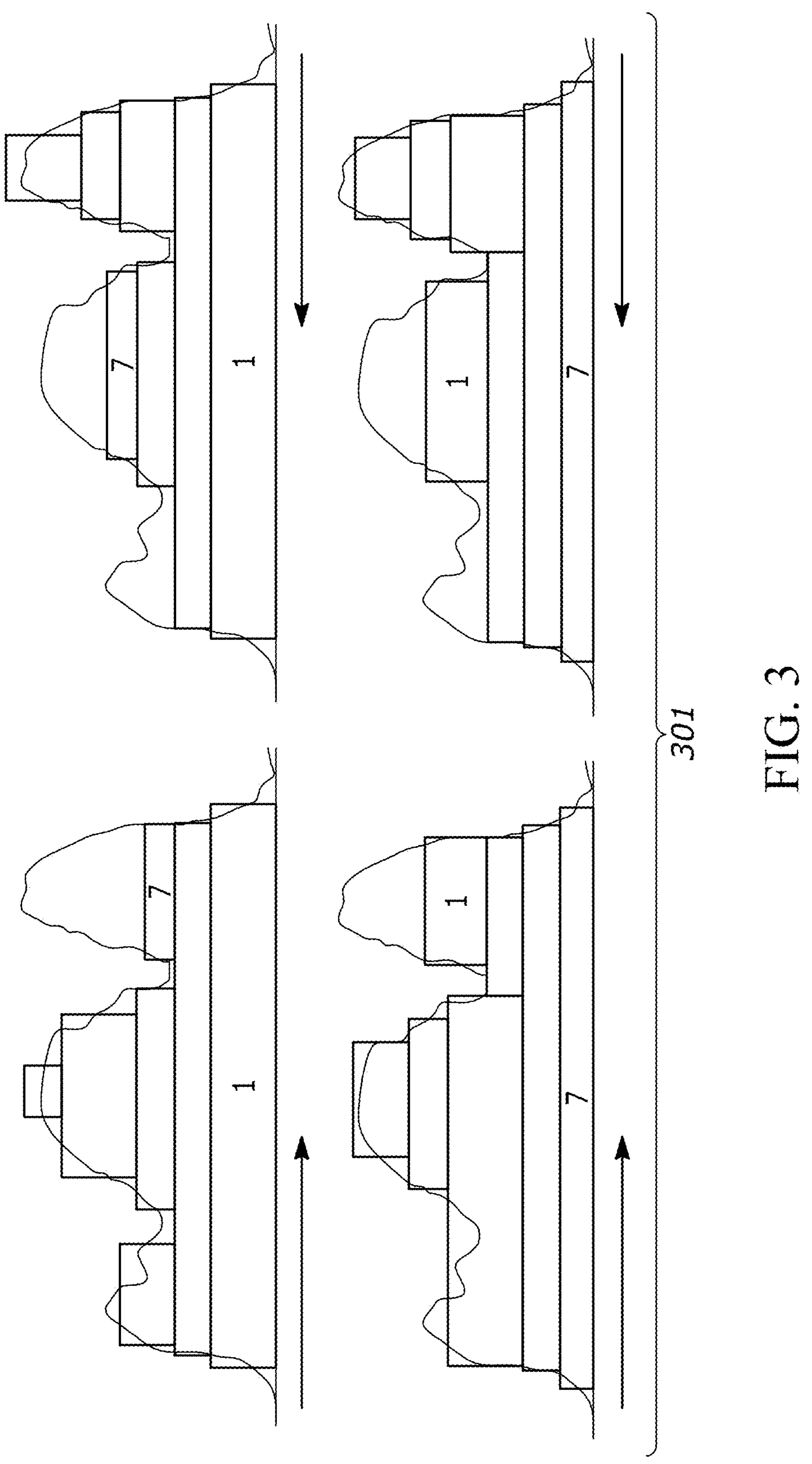
FIG. 3 comprises graphs as configured in accordance with various embodiments of these teachings.

By one approach, and referring to FIG. 3, half of the agents can be initialized using a stacked approach and half can be initialized using a sliding window approach. In this illustrative example, four examples 301 are presented depicting how a leaf can be fitted to the target fluence during the initial population generation. The rows illustrate two opposing control point orders (via the depicted numbers) and the columns illustrate two opposing fitting directions (via the depicted arrows).

The resulting initial population contains both agents that are already sufficiently close to acceptable solutions for the algorithm to converge quickly, and enough variation for the algorithm to converge to a good-quality global solution. If desired, the output of previous prior art iterations can also be included in the population. This means that the solution can be iteratively refined, and the iteration count can also be kept relatively small. That said, the initialization can also be easily extended with new types of initial agents when and as the latter become available.

In addition to mutating the agents, these teachings will also accommodate postprocessing the mutated agents (and the initial agents as well, if desired) before the cost calculation. This approach can serve to further enforce leaf movement limits (for example, during the last few iterations). The leaf positions can be represented as a sequence of position offsets (between adjacent control points) and the sequence can be gradually cropped (using a tightening threshold) so that offsets that violate any leaf-movement limits are eliminated. The back-transformed leaf sequence would in a general case potentially differ drastically from the original leaf sequence, but since movement limits are already (almost) fulfilled and the solution is gradually refined, such an approach does work as a postprocessing step.

Figure 4:
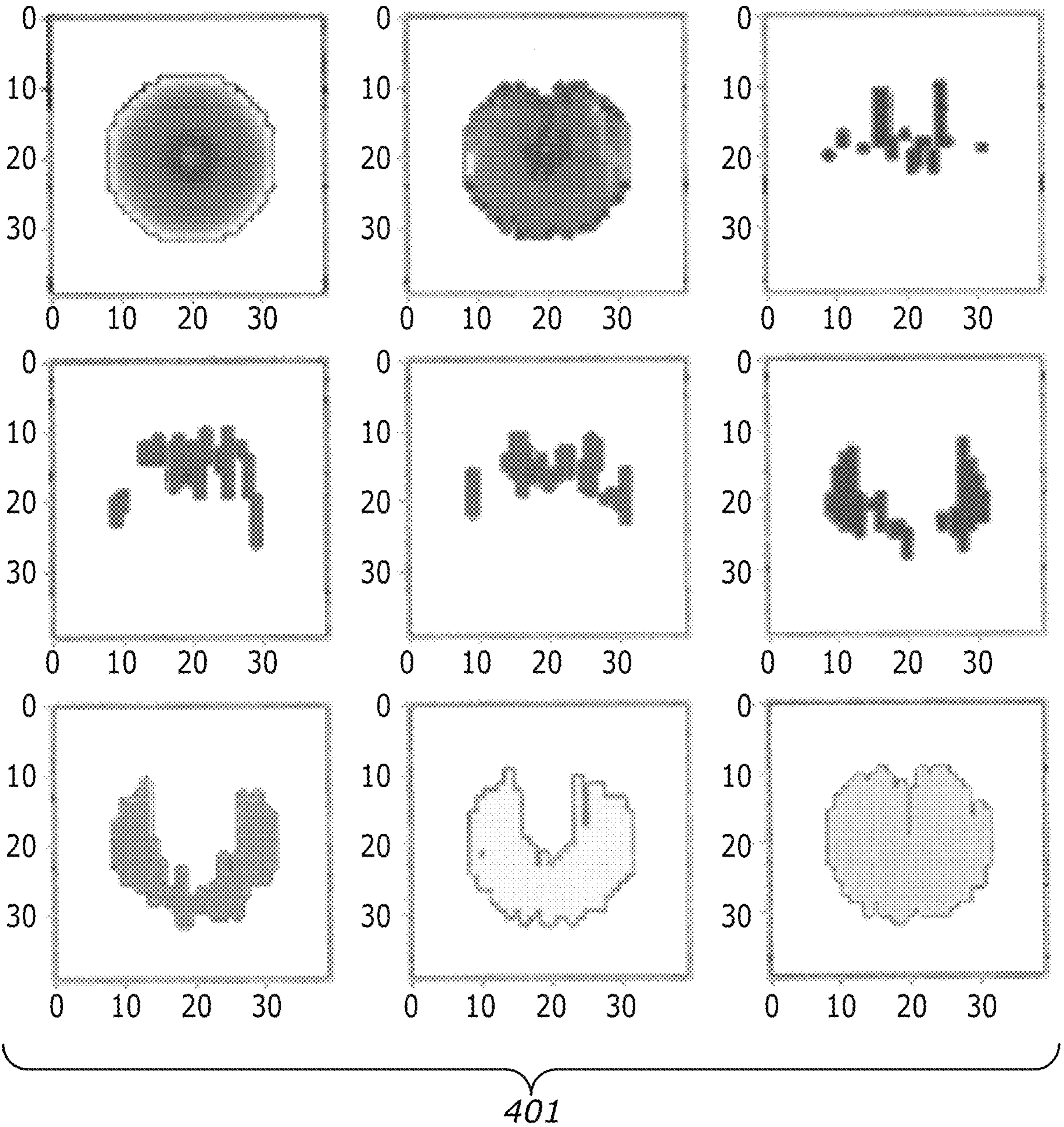
FIG. 4 comprises screenshots as configured in accordance with various embodiments of these teachings.

FIG. 4 presents an illustrative output 401 of the foregoing teachings based upon 100 iterations from a cold start with expressed leaf movement limits. From the top left corner, these illustrations present synthetic target fluence, output fluence (for 7 control points), and leaf opening and monitor units (that can be presented via the aforementioned user interface 103 using different colors as appropriate) in control points number 1 through number 7. (In this example, it is presumed that the leaves move vertically.)

While the prior art is typically configured to work on a single solution candidate that is gradually improved by mutating individual leaves using a complex mutation formula, the present teachings provide for working on a set of solution candidates that are mutated concurrently using what can be a simple mutation formula. So configured, these teachings are very suitable for GPU-acceleration. Furthermore, the foregoing teachings can serve to find a global optimal solution. In particular, the foregoing approaches can handle several peaks and valleys in the direction of movement of the leaves.

It will be appreciated that the foregoing teachings tend to be much simpler as compared to known solutions that rely on a complex mutation formula that imposes movement limits, whereas the foregoing can be configured to formulate movement limits as penalty terms that are part of the cost function. Penalty terms are much easier to understand, implement, and experiment with. New types of objectives, initial agents, and postprocessing steps can be readily added to the algorithm.

Parallel Explicit Integration Approach

As described above, these teachings will accommodate formulating a leaf sequencing problem in a form that is solvable by a parallel explicit integration approach. Parallel explicit integration approaches are known in the art and find use, for example, in molecular dynamics. With the foregoing in mind, the applicant has determined that one can generally analogize multi-leaf collimator leaf positions to atoms, target fluences to external force fields, and leaf movement constraints to interactions between atoms. An iterative solution step for leaf positions can accordingly correspond to a timestep in molecular dynamics (without simulating physical time).

In this example, the approach has the following main loop.

```
Loop over iterations {
  Loop #1 over leaves and control points {
    Calculate forces acting on leaves
  }
  Loop #2 over leaves and control points {
    Update leaf positions and fluence
  }
}
```

In the foregoing example, both subloops (1 and 2) parallelize over all optimization variables (the number of control points times the number of leaves in multi-leaf collimator), thereby making the scheme suitable for processing by a graphics processing unit. Forces acting on leaves can include, for example, forces derived from fluence under each leaf and from constraints between leaves in adjacent control points.

To derive forces from fluences, fluence can be assumed to be continuous (in contrast to the typical pixel image of fluence). The relevant fluence variable in this problem is difference fluence which is a difference between target fluence and current fluence produced by current leaf apertures.

Figure 5:
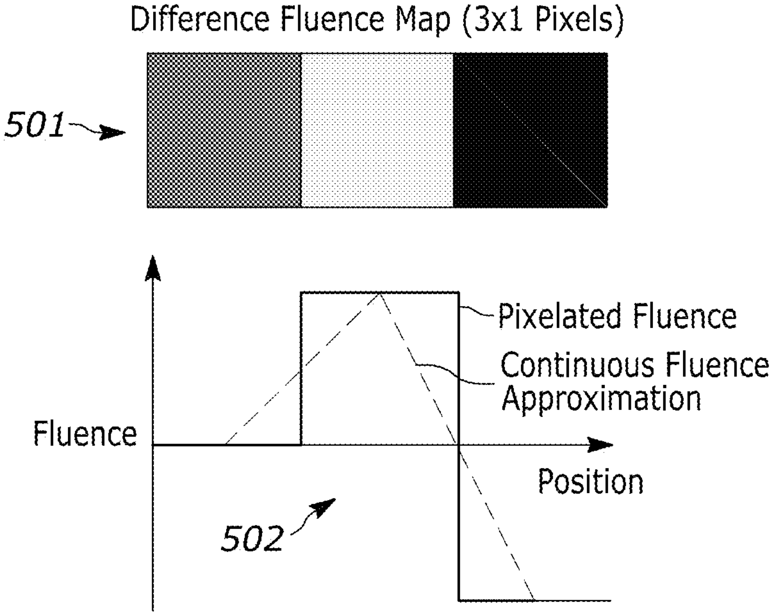
FIG. 5 comprises a pixel map and graph as configured in accordance with various embodiments of these teachings.

FIG. 5 illustrates the continuous fluence approximation. Force exerted from difference fluence to a leaf is fluence*mu, where mu is the monitor unit weight of the control point, in the direction of the leaf opening on positive difference fluence and closing on negative difference fluence. The difference fluence can be stored as a pixel map 501, but fluence value as function of leaf position can be approximated continuously via interpolation of pixel values as illustrated by the graph 502.

Figure 6:
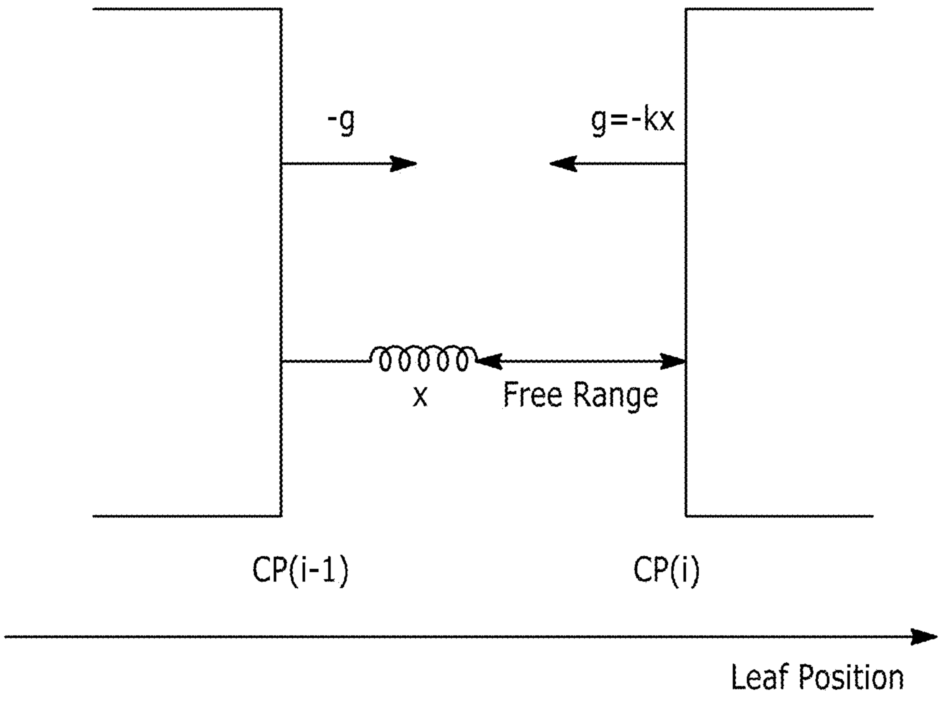
FIG. 6 comprises a schematic representation as configured in accordance with various embodiments of these teachings.

Constraints for leaf positions can include constraints between neighboring leaves in the multi-leaf collimator and leaf movement constraints between adjacent control points. The latter, leaf movement constraints, are illustrated in FIG. 6. In this example, movement between control points CP(i−1) and CP(i) is penalized by a stiff force if it exceeds a free range (where leaf movement by a distance x beyond a free range is opposed by a linear force g with stiffness k). Efficient implementation of leaf movement limits can be very beneficial to produce leaf sequences with optimal and controllable treatment delivery times.

After the forces have been calculated for each leaf, leaf positions can be updated from solution step t to t+1 using a symplectic (semi-explicit) Euler scheme:

$$\text{Velocity update:}\quad v_{t+1} = v_t + hg$$

$$\text{Position update:}\quad x_{t+1} = x_t + hv_{t+1}$$

where g is total force on a leaf and h is a small step size that can be defined by stiffness of the system, depending on fluence magnitude and stiffness of leaf movement and position penalties. The inclusion of velocities v in the solver can serve to speed up convergence and represents that leaves have inertia that can help them roll through flat regions and small local minima in the landscape of fluence and leaf constraint penalties. If desired, a damping force proportional to velocity can be included in subloop 1 referred to above.

At the end of subloop 2, difference fluence can be updated with new leaf positions. The iteration loop can be run until, for example, the leaves reach a new equilibrium. A sufficient fixed number of iterations can be used if desired to ensure sufficient convergence, or convergence criterion based on, for example, kinetic energy (represented, for example, by the sum of velocities squared) can be used.

In a direct aperture optimization application setting, the foregoing approaches can be called iteratively along with other functionality that serves to update target fluences, with successive rounds starting from the leaf positions resulting from the previous call.

So configured, leaf sequencing can be readily implemented on a graphics processing unit, making it possible, for example, to develop faster GPU-accelerated direct aperture optimizer. Complex interactions between leaves, and between leaves and fluence, are easier to implement as the force and update substeps are fully separable. It will also be appreciated that these teachings can be readily applied when optimizing leaves in an application setting that employs dual-layer multi-leaf collimators with only small changes likely being beneficial.

The leaf-movement optimization results so achieved can be used in the overall optimization of a radiation therapy treatment plan. The resultant optimized radiation treatment plan 113 can then be used in ordinary course to administer radiation to a patient using a corresponding radiation treatment platform 114.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method to facilitate optimizing a radiation treatment plan for a particular patient using at least one multi-leaf collimator, the method comprising:
  - optimizing leaf movements for the at least one multi-leaf collimator using a first control circuit configured as a graphics processing unit, wherein the graphics processing unit is configured to optimize the leaf movements as a function of
  - at least one parallel explicit integration approach, wherein the at least one parallel explicit integration approach comprises, at least in part:
  - determining forces acting on each leaf of the at least one multi-leaf collimator as a function, at least in part, of determined fluence under each of the leaves and from constraints between the leaves in adjacent control points; and
  - updating velocities and positions of the leaves as a function of the forces; and wherein the optimizing the leaf movements is configured as a highly parallel optimization opportunity.

2. The method of claim 1 further comprising:
  - configuring the optimizing the leaf movements as a highly parallel optimization opportunity by a second control circuit.

3. The method of claim 2 wherein the second control circuit is configured as a central processing unit.

4. The method of claim 1 wherein the graphics processing unit is configured to optimize the leaf movements as a function of both of:
  - at least one metaheuristic approach; and
  - the at least one parallel explicit integration approach.

5. The method of claim 4 wherein the graphics processing unit is configured to optimize the leaf movements as a function of first optimizing as a function of the at least one metaheuristic approach and subsequently optimizing as a function of the at least one parallel explicit integration approach.

6. The method of claim 4 wherein the at least one metaheuristic approach comprises, at least in part:
  - a differential evolution approach.

7. The method of claim 6 wherein the differential evolution approach includes use of differential evolution-specific parameters that include an iteration count of about 100 iterations and a population size of about 50 agents.

8. The method of claim 1 wherein fluence is assumed to be continuous when determining the forces.

9. An apparatus to facilitate optimizing a radiation treatment plan for a particular patient using at least one multi-leaf collimator, the apparatus comprising:
  - a first control circuit configured as a graphics processing unit configured to optimize leaf movements for the at least one multi-leaf collimator, wherein the graphics processing unit is configured to optimize the leaf movements as a function of at least one of:
  - at least one metaheuristic approach; and/or
  - at least one parallel explicit integration approach, wherein the at least one parallel explicit integration approach comprises, at least in part:
  - determining forces acting on each leaf of the at least one multi-leaf collimator as a function, at least in part, of determined fluence under each of the leaves and from constraints between the leaves in adjacent control points; and
  - updating velocities and positions of the leaves as a function of the forces; and wherein the graphics processing unit is configured to optimize the leaf movements as a highly parallel optimization opportunity.

10. The apparatus of claim 9 further comprising:

a second control circuit operably coupled to the first control circuit and configured to optimize the leaf movements as a highly parallel optimization opportunity.

11. The apparatus of claim 10 wherein the second control circuit is configured as a central processing unit.

12. The apparatus of claim 9 wherein the graphics processing unit is configured to optimize the leaf movements as a function of both of:

at least one metaheuristic approach; and the at least one parallel explicit integration approach.

13. The apparatus of claim 12 wherein the graphics processing unit is configured to optimize the leaf movements as a function of first optimizing as a function of the at least one metaheuristic approach and subsequently to optimize the leaf movements as a function of the at least one parallel explicit integration approach.

14. The apparatus of claim 12 wherein the at least one metaheuristic approach comprises, at least in part:

a differential evolution approach.

15. The apparatus of claim 14 wherein the differential evolution approach includes use of differential evolution-specific parameters that include an iteration count of about 100 iterations and a population size of about 50 agents.

16. The apparatus of claim 9 wherein fluence is assumed to be continuous when determining the forces.

* * * * *